(12) United States Patent
Mammen

(10) Patent No.: US 6,656,694 B2
(45) Date of Patent: Dec. 2, 2003

(54) METHOD FOR IDENTIFYING A LIGAND FOR A BIOLOGICAL SUBSTRATE

(75) Inventor: Mathai Mammen, San Mateo, CA (US)

(73) Assignee: Theravance, Inc., South San Francisco, CA (US)

( * ) Notice: Subject to any disclaimer, the term of this patent is extended or adjusted under 35 U.S.C. 154(b) by 12 days.

(21) Appl. No.: 09/758,916

(22) Filed: Jan. 11, 2001

(65) Prior Publication Data
US 2002/0090645 A1 Jul. 11, 2002

(51) Int. Cl.[7] .............. G01N 33/53; G01N 33/566; C07K 1/00; C07K 16/00; A61K 39/385
(52) U.S. Cl. .......... 435/7.1; 435/7.2; 435/DIG. 14; 436/501; 436/518; 530/345; 530/389.1; 530/402; 530/807; 424/1.11; 424/9.1; 424/178.1; 424/193.1
(58) Field of Search .......... 435/7.1, 7.2, DIG. 14; 436/501, 518; 530/345, 389.1, 402, 807; 424/1.11, 9.1, 178.1, 193.1

(56) References Cited

U.S. PATENT DOCUMENTS 5,401,636 A    3/1995   Craig
5,698,401 A   12/1997   Fesik et al.

FOREIGN PATENT DOCUMENTS

| EP | 0315 317 A2 | 5/1989 |
| WO | WO 97/35202 | 9/1997 |
| WO | WO 97/37223 | 10/1997 |
| WO | WO 99/25384 | 5/1999 |
| WO | WO99/42476 | 8/1999 |
| WO | WO99/64032 | 12/1999 |
| WO | WO00/00823 | 1/2000 |

OTHER PUBLICATIONS

S. Borman, C&EN Oct. 9, 2000 48–53.

*Primary Examiner*—Maurie Garcia Baker
(74) *Attorney, Agent, or Firm*—Jeffrey A. Hagenah; Martin A. Hay

(57) ABSTRACT

A method of identifying a ligand for a second binding site (5) on a biological substrate (1) is disclosed. The method comprises determining the effect of a candidate compound (9) on the binding of a probe compound (2) which binds to a first binding site (3) on the biological substrate in the presence of a first multibinding compound (4) which binds to the first (3) and second (5) binding sites on the biological substrate (1).

13 Claims, 2 Drawing Sheets

METHOD FOR IDENTIFYING A LIGAND FOR A BIOLOGICAL SUBSTRATE

BACKGROUND OF THE INVENTION

1. Field of the Invention

The present invention relates to a method for identifying compounds having biological activity. More particularly, it relates to a method of identifying a ligand that binds to a biological substrate.

2. State of the Art

The function of a biological system may be modulated by the action of a ligand that binds to a biological substrate in the system, and so elicits a biological response. The ligand may mimic the action of an endogenous ligand, in which case it is referred to as an agonist, or it may block the action of an endogenous ligand, in which case it is referred to as an antagonist. Many biologically useful compounds, such as pharmaceuticals, pesticides and plant growth regulators, work as ligands in this way.

It is very important that a ligand binds selectively to a biological substrate, and so does not elicit a biological response in any other biological system. It is also important that the ligand binds strongly to the biological substrate, so that only a small concentration of the ligand is required to elicit the biological response.

Over the course of time, biological systems have evolved in which the endogenous ligands bind strongly and selectively to their respective biological substrates.

Methods for identifying exogenous ligands that bind strongly and selectively to a biological substrate have been developed, but these methods are time-consuming and require the making and testing of large numbers of candidates.

One method involves measuring the ability of candidates to elicit a biological response in a test biological system, and then evaluating the selectivity of an active candidate by measuring its ability not to elicit a biological response in another biological system, or in a whole organism.

Another method involves measuring the ability of a candidate to displace a known ligand, such as the endogenous ligand or an agonist. In this method, the known ligand is used as a probe. It may be radiolabelled, so as to facilitate measuring the amount of the known ligand that is bound or unbound to the biological substrate in the presence and absence of the candidate.

Another method for identifying a ligand is disclosed in U.S. Pat. No. 5,698,401 (Fesik). This method makes use of a $^{15}N$ labeled biological substrate and an NMR technique. In the method, a $^{15}N/^{1}H$ two dimensional correlation spectrum of a biological substrate in the presence of a candidate is compared with a $^{15}N/^{1}H$ two dimensional spectrum in the absence of a candidate. By comparing the spectra obtained at different concentrations of the candidate, a dissociation constant, $K_d$, between the biological substrate and the candidate may be determined.

International patent application, Publication No. WO 00/00823 discloses a method of identifying a ligand in which a biological substrate that contains a chemically reactive group (or has been modified to contain a chemically reactive group) is exposed to a test compound capable of reacting with the chemically modified group. The method assumes that a test compound that possesses binding affinity for the biological substrate will tend to react more favorably with the chemically reactive group that a test compound that does not possess binding affinity.

Biological substrates may contain more than one site to which a ligand may bind.

Recently, interest has been growing in ligands that have the ability to bind to more than one binding site on a biological substrate (Borman, S., Oct. 9, 2000, C&EN, 48–53). Such ligands are referred to as multibinding or multivalent compounds or ligands. These multibinding ligands comprise two or more binding regions connected by one or more linkers. The linkers constrain the relative positions and orientations of the binding regions, so that each binding region can bind at the same time to the respective binding sites on the biological substrate. The biological substrate may be made up of a single unit or a cluster of two or more units, in which case a multivalent compound may bind simultaneously to binding sites on two or more units.

Multibinding ligands bind more strongly and selectively to biological substrates than monovalent ligands. This is because the presence of multiple binding regions means that it is less likely that the whole ligand will become unbound, and because it is less likely that two different biological substrates will possess the same multiple binding sites in the same relative positions.

WO 99/42476 and WO 99/64032 disclose an iterative method for identifying multibinding ligands in which candidates are prepared by connecting a diversity of fragments of known ligands through a diversity of linkers, then determining whether the candidates possess multibinding properties. A successful candidate will contain fragments of known ligands that are capable of binding to different binding sites on the biological substrate and are presented by the linker in such a way that they may bind simultaneously to their respective binding sites.

Application of the method disclosed in WO 99/42476 and WO 99/64032 has enabled the rapid identification of highly potent and selective ligands. However, there remains a need for other methods.

SUMMARY OF THE INVENTION

A method has now been devised for identifying ligands that makes use of the binding affinity of a ligand for one binding site on a biological substrate to identify a ligand that binds to another.

According to one aspect, therefore, the present invention provides a method of identifying a ligand for a second binding site on a biological substrate, which comprises determining the effect of a candidate compound on the binding of a probe compound which binds to a first binding site on the biological substrate in the presence of a first multibinding compound which binds to the first and second binding sites on the biological substrate.

A successful candidate compound will compete with the first multibinding compound for binding to the second binding site, and so reduce the binding of the first multibinding compound to the biological substrate. This reduced binding of the first multibinding compound may be detected by the increased binding of the probe compound.

Thus, in another aspect, the present invention provides a method of determining whether a candidate compound is a ligand for a second binding site of a biological substrate, the method comprising:

(a) contacting a biological substrate comprising a first binding site and a second binding site with a candidate compound in the presence of (i) a probe compound which binds to the first binding site of the biological substrate and (ii) a first multibinding compound which binds to the first binding site and the second binding site of the biological substrate;

(b) determining the amount of probe compound that binds to the first binding site of the biological substrate in step (a);

(c) comparing the amount of probe compound determined in step (b) with a pre-determined amount of probe compound that binds to the first binding site when the biological substrate is contacted with the probe compound and the first multibinding binding compound in the absence of the candidate compound.

If the candidate compound is a ligand for the second binding site of the biological substrate, more of the probe compound will bind to the first binding site of the biological substrate in the presence of the candidate compound than in its absence.

Additionally, the relative binding affinities of candidate compounds can be determined using the method of this invention by comparing the relative amounts of the probe compound that bind to the biological substrate in the presence of each of the candidate compounds. Therefore, in yet another aspect, the present invention provides a method of determining the relative binding affinity of a plurality of candidate compounds for a second binding site of a biological substrate, the method comprising:

(a) contacting a biological substrate comprising a first binding site and a second binding site with each of a plurality of candidate compounds in the presence of (i) a probe compound which binds to the first binding site of the biological substrate and (ii) a first multibinding compound which binds to the first binding site and the second binding site of the biological substrate;

(b) determining the amount of probe compound that binds to the first binding site of the biological substrate for each of the candidate compounds in step (a);

(c) comparing the amount of probe compound determined in step (b) for each of the candidate compounds.

Since the amount of probe compound that binds to the first binding site of the biological substrate in the presence of each candidate compound is related to that candidate compound's affinity for the second binding site, the relative affinity of each candidate compound for the second binding site can be determined.

DETAILED DESCRIPTION OF THE INVENTION

Figure 1:
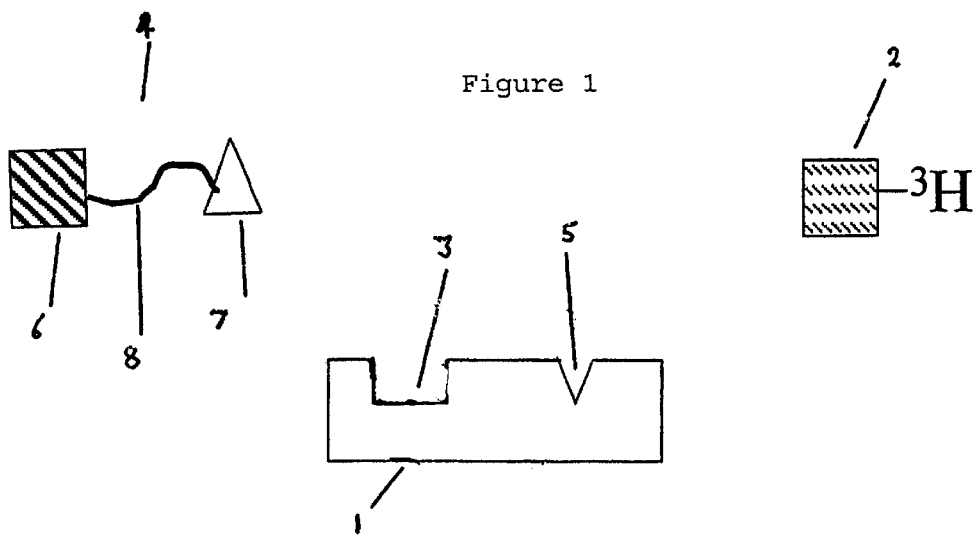
FIG. 1 shows a representation of a biological substrate (1), a radiolabeled probe compound (2) and a first multibinding compound (3).

The present invention provides a method of identifying a ligand for a second binding site on a biological substrate using a first multibinding compound and a probe compound.

Preferably, the first multibinding compound binds weakly to the second binding site on the biological substrate. It will then be easier for a candidate compound to displace the compound from the biological substrate. The more strongly the first multibinding compound binds to the second binding site, the higher the concentration of candidate compound required to displace it.

The biological substrate may be any biological material that contains first and second binding sites. It may be made up of a single unit or a cluster of two or more adjacent units, each of which may contain one or more binding sites (i.e., the first and second binding sites may be on the same or different biological substrates or units). Thus, for example, a biological substrate may be made up of one, two, three, four, five or more units and may contain from 2 to 100 binding sites.

The biological substrate may comprise, for example, a biopolymer such as a protein, carbohydrate or nucleic acid.

The biological substrate is preferably a membrane receptor, a membrane channel (ion channel), an enzyme or a macromolecule. An example of a biological substrate is the muscarinic M2 receptor.

The biological substrate may be bound to a membrane and may be obtained by a known method, for example by a recombinant technique.

The probe compound may be, for example, radiolabeled, fluorescent or chemiluminescent. The radiolabel may be, for example, tritium ($^3$H).

Substances suitable for use as probe compounds for a given biological substrate are well known in the art. Typically, the $K_d$ of the probe compound is less than 100 nM, preferably less than 10 nM. For example, tritiated N-methyl scopalamine may be used as a probe compound for the muscarinic M2 receptor.

The first multibinding compound, and its ability to bind to the first and second sites on the biological substrate, may be known from the art. If no first multibinding compound is known, a suitable first compound may be derived as follows:

If it is known in the art, for example from X-ray crystallography, that a biological substrate contains first and second binding sites separated by a known distance, and ligands for each binding site are known, then first multibinding compounds may be identified by connecting fragments of the ligands though a linker. The linkers may be, for example, unbranched or branched alkyl or ether chains, optionally containing one or more carbon—carbon double or triple bonds. Examples of methods for identifying first multibinding compounds where the required ligands are known may be found, for example, in WO 99/42476 and WO 99/64032.

The effect of a candidate compound on the binding of a probe compound may conveniently be determined by using a technique known in the art. For example, when the probe compound is radiolabeled, the effect may be determined by measuring the radioactivity from bound probe compound with and without exposure to the candidate compound. A successful candidate compound will reduce the amount of the radiolabeled probe compound displaced by the first multibinding compound by reducing the binding of the first compound to the biological substrate, so making it easier for the radiolabeled probe compound to compete with the first multibinding compound for binding to the second binding site on the biological substrate. As a consequence, the radioactivity from bound probe compound will be higher with exposure to the candidate compound than without.

The effects of each candidate compound can be measured separately, or the effects of a plurality of candidate compounds can be measured in a multi-well plate. A convenient multi-well plate is a 96, 384 or 1536 well plate. The candidate compounds can be screened individually in separate wells, or as groups, each group in one well. If a group of candidate compounds shows good binding, the members of the group may then be evaluated individually. Initial screening of groups of candidate compounds instead of individual candidate compounds may considerably accelerate the screening process, and facilitate the screening of libraries of candidate compounds generated by combinatorial chemistry techniques or of natural product mixtures (for example prepared by fermentation or extracted from organisms, such as plants).

In the method, the first multibinding compound is conveniently present at a concentration in the range of from 5 to 10 times the Kd of the first multibinding compound. At this concentration, the probe compound is significantly displaced. If, for example, the probe compound is radiolabeled, very little radioactivity is detected in a well containing only the first multibinding compound and the probe compound.

The probe compound is conveniently present at a concentration less than the Kd of the probe compound.

The candidate compound is conveniently present at a concentration in the range of from 100 to 500 $\mu$M.

The candidate compounds may be selected randomly for testing, for example from a diverse collection of compounds. Alternatively, candidate compounds may be selected based upon their structural similarity with the region of the first multibinding compound that binds to the second site. For example, if the region of the first multibinding compound that binds to the second site is an amine, other amines may be selected as candidate compounds. "A plurality of candidate compounds" refers to two or more, preferably 2 to 100; more preferably, 2 to 20 candidate compounds.

A successful candidate compound may turn out to be a potent and selective ligand for the biological substrate in its own right. If it is not, then the following steps may be taken.

Once a successful candidate compound has been identified, a second compound is prepared that is capable of binding to the first binding site on the biological substrate and contains a fragment of the candidate compound. The fragment and its position in the second compound are chosen with the aim of finding a ligand that binds to the first and second binding sites on the biological substrate, preferably with a potency that exceeds that of the first multibinding compound.

According to one preferred aspect, therefore, the method further comprises preparing a second compound that is capable of binding to the first binding site on the biological substrate and contains a fragment of the candidate compound, and determining the binding of the second compound to the biological substrate.

It will be appreciated that a candidate compound as a whole cannot be incorporated into the second compound, because at least one atom on the candidate compound must be removed in order to covalently link the candidate compound to the second compound. For example, when the candidate compound is of the formula X-H, the fragment may be of the formula X.

It will also be appreciated that parts of the structure of a successful candidate compound may contribute little or nothing to the binding of the candidate compound to the biological substrate. Accordingly, for a second compound to bind to the second site on the biological substrate, the fragment of the candidate compound will need to contain parts of the structure of the candidate compound that contribute to binding. Moreover, in order for the second compound to bind to both the first and second sites on the biological substrate, the fragment will need to be positioned correctly.

Thus, for example, the structures of the first multibinding and second compounds may be represented by formulae I and II respectively:

$$R^{1a}-L^{a}-R^{2a} \qquad \text{I}$$

$$R^{1b}-L^{b}-R^{2b} \qquad \text{II}$$

in which:

$R^{1a}$ and $R^{1b}$ each represents an organic group that contains a fragment capable of binding to the first binding site on a biological substrate;

$R^{2a}$ represents an organic group containing a fragment capable of binding to the second binding site on a biological substrate, $L^a$ represents a linker group that orients the groups $R^{1a}$ and $R^{2a}$ in the correct position to permit binding of both $R^{1a}$ and $R^{1b}$ to the respective first and second binding sites on the biological substrate;

$R^{2b}$ represents an organic group containing a fragment of a successful candidate compound; and $L^b$ represents a linker group that constrains the relative positions of $R^{1b}$ and $R^{2b}$.

An example of a first multibinding compound of formula I which binds to the first and second binding sites on the muscarinic M2 receptor is a compound of formula:

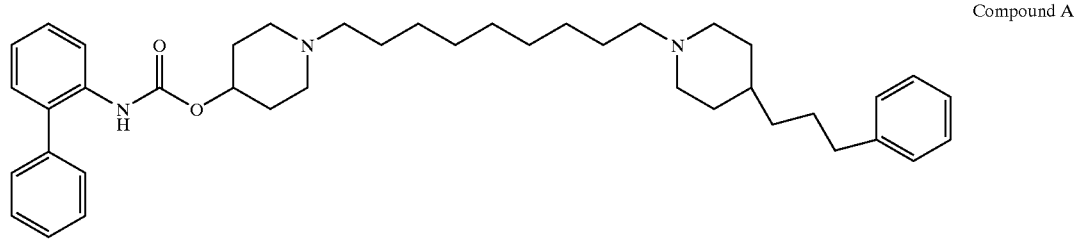

Compound A

Conveniently, $R^{1b}$ is the same as $R^{1a}$.

If the formula of a successful candidate compound is X-H, $R^{2b}$ may be, for example, X $L^b$ may in some cases be the same as $L^a$, for example when $R^{2b}$ is X.

An example of a candidate compound of formula H-X is a compound of formula

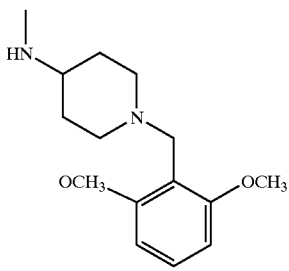

Compound C

Accordingly, the second compound may be, for example, of the formula:

$R^{1a}-L^a-X$   II'

Thus, an example of a compound of formula II' is a compound of formula:

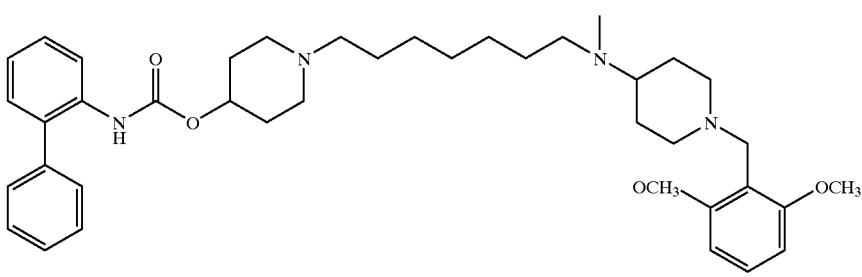

Compound D

The parts of the structure of the candidate compound that contribute to binding may be determined by conducting a structure activity relationship study using a probe compound, a first multibinding compound and a plurality of candidate compounds, as described herein. In the structure activity relationship study, the structures of the candidate compounds may be varied systematically to determine which parts of the structure are important for binding. From the results of this study, it should also be possible to determine the points on the fragment that may be attached to the residue of the residue of the second compound.

Preferably, a plurality of different second compounds is prepared, and the binding of each to the biological substrate is determined. The plurality of second compounds may comprise, for example, different fragments or the same fragments attached through different positions on the fragment.

Conveniently, the candidate compounds are selected such that the second compounds can be prepared in the same way as the first multibinding compound. For example, if the first compound can be prepared by the following process (A):

$R^{1a}-L^{a'}-Z^1+H-R^{2a}->R^{1a}-L^a-R^{2a}$ in which $Z^1$ represents a chemically reactive group, then candidate compounds of formula H-X are selected that may be used to prepare second compounds by an analogous process:

$R^{1a}-L^{a'}-Z^1+H-X->R^{1a}-L^a-X$

For example, $H-R^{2a}$ and each candidate compound of formula H-X may represent amines, and $Z^1$ may represent a leaving atom or group, such as a halogen atom or an organosulfonyloxy group.

Alternatively, if the first multibinding compound can be prepared by the following process (B):

$R^{1a}-L^a-H+Z^2-R^{2a'}->R^{1a}-L^a-R^{2a}$ in which $Z^2$ represents a chemically reactive group, then candidate compounds of formula H-X are selected such that second compounds can be prepared by an analogous process:

$R^{1a}-L^a-H+Z^2-X'->R^{1a}-L^a-X$

It will be appreciated that in both cases, the relative positions of the binding regions of the second compounds are preserved relative to their positions in the first compounds, which enhances the probability that the second compounds will bind to both the first and second binding sites on the biological substrate. It will also be appreciated that in process (A), the starting material is the candidate compound itself, hence this process is preferred.

Once a second multibinding compound has been found that binds to both the first and second binding sites on the biological substrate, this second multibinding compound may be used together with a probe compound that binds to the second binding site in order to identify other ligands for the first binding site on the biological substrate. These other ligands may in turn be used to identify further compounds that bind to the first and second binding sites on the biological substrate. Thus, starting from a first multibinding compound that binds to first and second sites on a biological substrate, the method according to the invention may be used to optimize binding to the biological substrate by providing replacements for the regions of the first multibinding compound that bind respectively to the first and to the second binding regions.

It will also be appreciated that although the invention has been described in detail with particular reference to the identification of divalent compounds, there is in principle no limit to the valency of the multibinding compounds that may be identified by the method according to the invention. For example, the first multivalent compound and/or the second compounds may have a valency of from 2 to 100. Thus the method according to the invention may further comprise preparing a third compound that is capable of binding to the first and second binding sites on the biological substrate and containing a fragment of a compound capable of binding to a third binding site on the biological substrate, and determining the binding of the third compound to the biological substrate.

The invention will now be described in more detail with reference to the drawings.

FIG. 1 shows a representation of a biological substrate (1), a radiolabeled probe compound (2) that binds to a first site (3) on the biological substrate, a first multibinding compound (4) that binds to the first binding site (3) and a binding second site (5) on the biological substrate. The first multibinding compound contains a first binding region (6)

that binds to the first site on the biological substrate, a second binding region (7) that binds to the second site on the biological substrate, and a linker (8) that connects the first and second regions.

Figure 2:
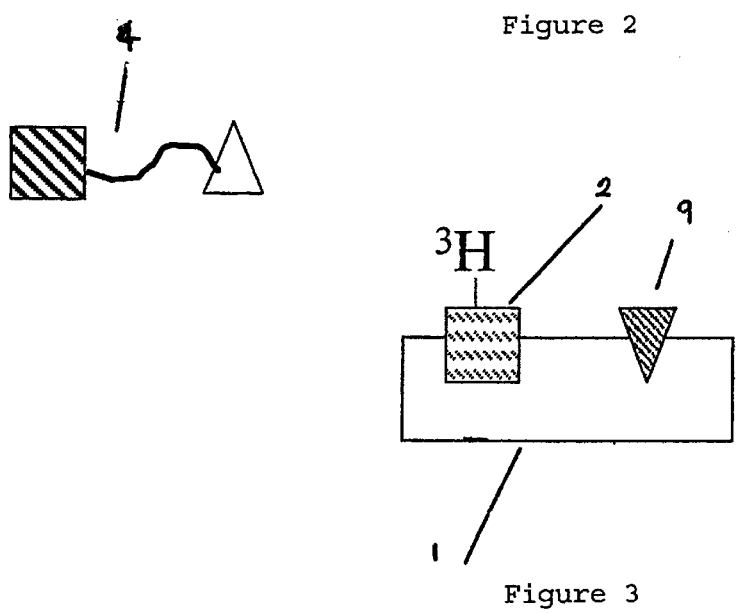
FIG. 2 shows a representation of a biological substrate (1), a radiolabeled probe compound (2), a first multibinding compound (3) and a candidate compound (9); where the radiolabeled probe compound and the candidate compound are bound to the biological substrate.

FIG. 2 shows a representation of a biological substrate (1), a radiolabeled probe compound (2) that binds to a first site (3) on the biological substrate, a first multibinding compound (4) that binds to the first site (3) and a second site (5) on the biological substrate and a candidate compound (9) that binds strongly to the second binding site (5) on the biological substrate. The candidate compound has displaced the first multibinding compound from the biological substrate, and the probe compound (2) has bound to the first binding site on the biological substrate.

Figure 3:
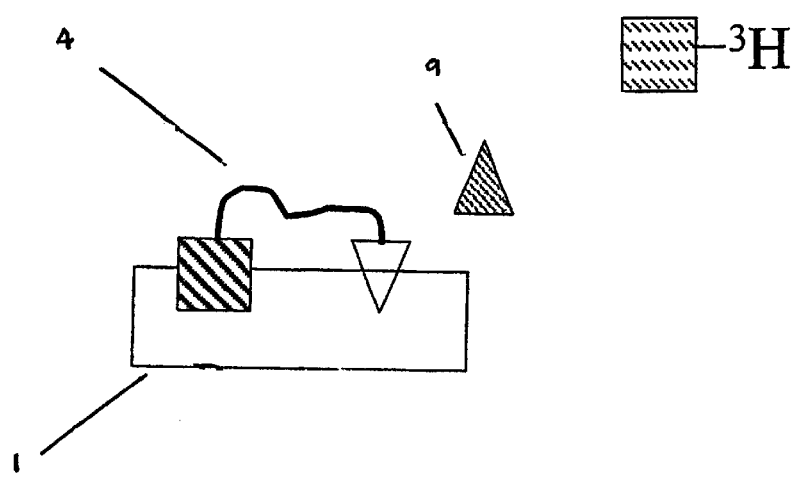
FIG. 3 shows a representation of a biological substrate (1), a radiolabeled probe compound (2), a first multibinding compound (3) and a candidate compound (9); where the first multibinding compound is bound to the biological substrate.

FIG. 3 shows a representation of a biological substrate (1), a radiolabeled probe compound (2) that binds to a first site (3) on the biological substrate, a first multibinding compound (4) that binds to the first site (3) and a second site (5) on the biological substrate and a candidate compound (10) that binds weakly to the second binding site (5) on the biological substrate. The candidate compound has not displaced the first multibinding compound from the biological substrate, so the probe compound (2) is not bound to the first binding site on the biological substrate.

Figure 4:
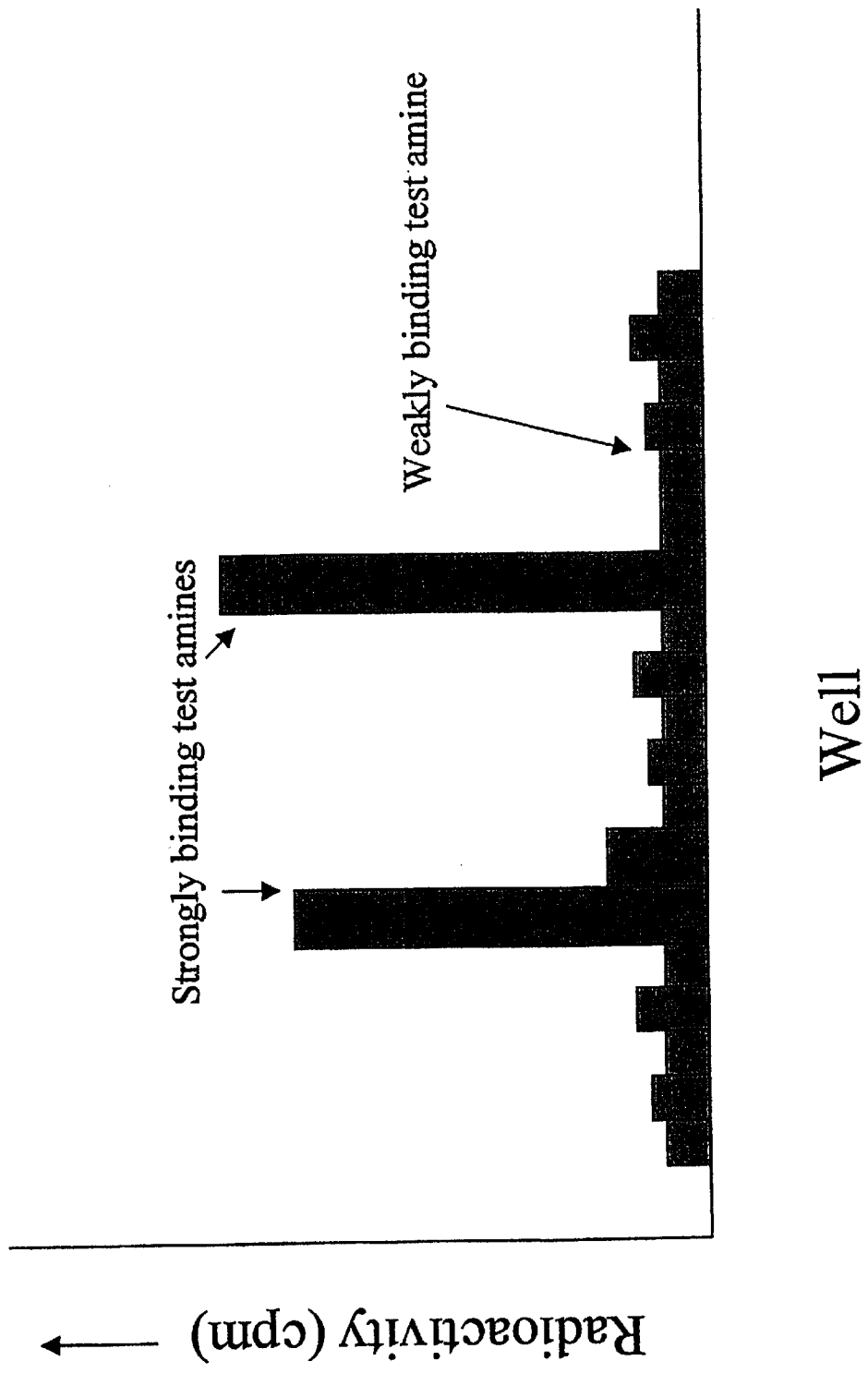
FIG. 4 shows a plot of radioactivity measured after candidate compounds have been added to each well, and the biological substrate has been separated by filtration from any unbound contents of the well.

After the candidate compounds have been added to the wells, the contents are incubated, then the biological substrates are separated from the unbound contents of the wells by filtration. The radioactivity emitted from the biological substrates is then measured. FIG. 4 depicts the radioactivity that is measured for different candidate compounds. Candidate compounds that bind strongly to the second binding site of the biological substrate cause high binding of the probe compound to the biological substrate, resulting in a high measured level of activity. Candidate compounds that bind weakly produce a low level of radioactivity.

EXAMPLES

The following Examples illustrate the invention.

Example A

Synthesis of 4-Piperidyl N-(2-Biphenyl)carbamate

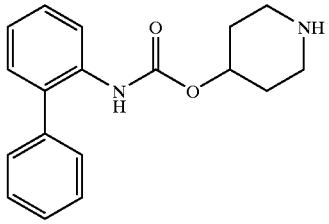

Step 1: In a 50 mL sealed tube was added 2-biphenylylisocyanate (8 g, 41 mmol) in anhydrous acetonitrile (40 mL). To this solution was added N-benzyl-4-piperidinol (9.8 g, 51.25 mmol) and the tube was partially immersed in a silicon oil bath and heated to 85° C. After 16 h, the reaction mixture was cooled and concentrated in vacuo to give a 1-benzyl-4-piperidyl N-(2-biphenyl) carbamate which was used in the next step without further purification.

Step 2: 1-Benzyl-4-piperidyl N-(2-biphenyl)carbamate (12.5 g, 32.3 mmol) was dissolved in anhydrous methanol (150 mL) and formic acid (25 mL, 660 mmol) and the solution was flushed with gaseous nitrogen for 15 min. 10% Palladium on carbon (3 g) was added and the reaction mixture was stirred under nitrogen atmosphere. After 18 h, the reaction mixture was filtered through Celite and the filtrate was concentrated to give a yellow solid. The solid was partitioned between 0.1 N hydrochloric acid (300 mL) and diethyl ether (300 mL). The aqueous layer was washed with diethyl ether and then made basic with 1 N sodium hydroxide solution to pH 12. A white solid precipitated which was extracted into ethyl acetate. The ethyl acetate layer was dried over magnesium sulfate and evaporated to dryness to give 4-piperidyl N-(2-biphenyl)carbamate as a colorless solid (6.63 g, 69%). MS=296.9 MH+.

Example B

Synthesis of Compound A

A mixture of 4-piperidyl N-(2-biphenyl)carbamate (1.95 g, 6.60 mmol), and 1,9-dibromononane (1.34 mL., 6.60 mmol) in acetonitrile (45 mL.) are heated to 80° C. After 1 h, 4-(3-phenylpropyl)piperidine (1.33 g, 6.60 mmol) is added to the reaction mixture and heating is continued. After 4 h, the reaction mixture is cooled and concentrated under reduced pressure and purified by HPLC to yield the desired product.

Example 1

Screening of Candidate Compounds

Into each well in a 96 well place, the following are added:

a) Compound A, such that the final concentration in the well is 200 nM (10 times the Kd of Compound A) in phosphate buffered saline at pH 7.4;

b) tritiated N-methyl scopalamine ($^3$H-NMS), such that the final concentration in each well is 10 nM (0.5 times the Kd of $^3$H-NMS);

c) a candidate compound at a final concentration of 500 nM, the candidate compound being selected from amines including Compound B and Compound C (which are commercially available);

Compound B

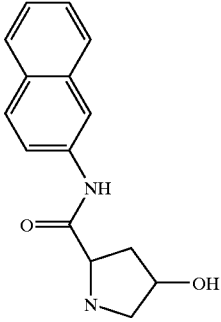

-continued

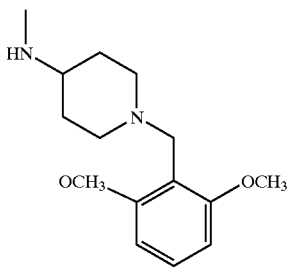

Compound C and d) membrane containing human cloned muscarinic receptor (prepared by expressing M2 coding plasmid in CHO cells using well-known procedures and reagents).

The 96 well plate is then incubated for 1 hour at 37° C. After incubation, the membranes are filtered to separate bound from unbound $^3$H-NMS. Scintillant is then added, and the plate is placed in a counter to measure the radioactivity in each well.

The amount of radioactivity determined for each well is then compared to a pre-determined amount of radioactivity measured using the above procedure in the absence of a candidate compound. A well containing a successful candidate compound (i.e., a ligand for the second binding site of the receptor) exhibits higher radioactivity relative to the amount of radioactivity measured in the absence of a candidate compound.

Additionally, the amount of radioactivity in wells containing a more successful candidate compound (i.e. a compound having greater affinity for the second binding site) is higher than the amount of radioactivity in wells containing a less successful or unsuccessful candidate compound, because the more successful candidate compound has displaced more of Compound A from the receptor, so allowing more $^3$H-NMS to bind instead. In the above procedure, Compound B is found to bind weakly to the receptor (lower radioactivity observed) relative to Compound C, which is found to bind strongly (higher radioactivity observed).

Compound D is then prepared from Compound C by a method analogous to that used to prepare Compound A.

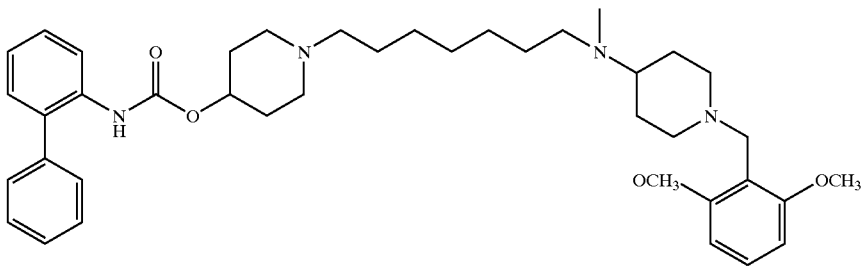

Compound D

The binding of Compound D to the receptor is then measured using $^3$H-NMS. Compound D is found to have a Kd of 2 nM, which is more potent than Compound A.

What is claimed is:

1. A method of identifying a ligand for a second binding site on a biological substrate, which comprises
determining the effect of a candidate compound on the binding of a probe compound which is known to bind to a first binding site on the biological substrate, in the presence of a first multibinding compound which is known to bind to the first and second binding site on the biological substrate, whereby the candidate compound may compete with the first multibinding compound for binding to the second binding site, so reducing the binding of the first multibinding compound to the biological substrate and so increasing the binding of the probe compound to the first binding site; and
identifying as a ligand for the second binding site of the biological substrate a candidate compound that has the effect of increasing the binding of the probe compound to the first binding site of the biological substrate.

2. The method of claim 1, in which the first multibinding compound binds weakly to the second binding site on the biological substrate.

3. The method of claim 1, in which the probe compound is radiolabeled.

4. The method of claim 3, in which the effect of the candidate compound is determined by measuring the radioactivity from bound probe compound with and without exposure to the candidate compound.

5. The method of claim 1 wherein the first multibinding compound is present at a concentration in the range of from 5 to 10 times the Kd of the first multibinding compound.

6. The method of claim 1, in which the probe compound is present at a concentration less than the $K_d$ of the probe compound.

7. The method of claim 1, in which the candidate compound is present at a concentration in the range of from 100 to 1000 $\mu$M.

8. The method of claim 1, in which the effects of a plurality of candidate compounds are measured in a multiwell plate.

9. A method of determining whether a candidate compound is a ligand for a second binding site of a biological substrate, the method comprising:
(a) contacting a biological substrate comprising a first binding site and a second binding site with a candidate compound or a plurality of candidate compounds in the presence of (i) a probe compound which is known to bind to the first binding site of the biological substrate and (ii) a first multibinding compound which is known to bind to the first binding site and the second binding site of the biological substrate, whereby the candidate compound may compete with the first multibinding compound for binding to the second binding site, so reducing the binding of the first multibinding compound to the biological substrate and so increasing the binding of the probe compound to the first binding site;
(b) determining the amount of probe compound that binds to the first binding site of the biological substrate in step (a);
(c) comparing the amount of probe compound determined in step (b) with a pre-determined amount of probe compound that binds to the first binding site when the biological substrate is contacted with the probe compound and the first multibinding binding compound in the absence of the candidate compound or compounds, and identifying as a ligand for a second binding site of the biological substrate a candidate compound that has the effect of increasing the binding of the probe compound to the first binding site of the biological substrate.

10. The method of claim 9, wherein the probe compound is radiolabeled, fluorescent or chemiluminescent.

11. The method of claim 9, wherein the first multibinding compound is present at a concentration in the range of from 5 to 10 times the Kd of the first multibinding compound.

12. The method claim 9, wherein the probe compound is present at a concentration less than the $K_d$ of the probe compound.

13. The method of claim 9, wherein the candidate compound is present at a concentration in the range of from 100 to 1000 $\mu$M.

* * * * *